# (12) United States Patent
Motomiya et al.

(10) Patent No.: US 7,235,525 B2
(45) Date of Patent: Jun. 26, 2007

(54) AGENT FOR TREATMENT OF METABOLIC BONE DISEASE

(75) Inventors: Yoshihiro Motomiya, Kashihara (JP); Yoshiyuki Moriguchi, Toshima-ku (JP); Hiroyuki Ohkawa, Toshima-ku (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/516,688

(22) PCT Filed: Jun. 6, 2003

(86) PCT No.: PCT/JP03/07198

§ 371 (c)(1), (2), (4) Date: Dec. 6, 2004

(87) PCT Pub. No.: WO03/103703

PCT Pub. Date: Dec. 18, 2003

(65) Prior Publication Data

US 2005/0176635 A1    Aug. 11, 2005

(30) Foreign Application Priority Data

Jun. 6, 2002    (JP)    ............................. 2002-165544

(51) Int. Cl.
*A61K 38/00*    (2006.01)
*C07K 14/505*    (2006.01)

(52) U.S. Cl. .......................................... 514/2; 530/395
(58) Field of Classification Search .................... None
See application file for complete search history.

(56) References Cited

U.S. PATENT DOCUMENTS

2002/0061849 A1 *    5/2002    Nielsen et al. ................. 514/12

FOREIGN PATENT DOCUMENTS

EP    0 499 242 A1    8/1992

OTHER PUBLICATIONS

Abendroth et al. Erythropoietin enhances histomorphometric signs of renal osteodystrophy. Bone (1997) vol. 20, No. 4 Suppl., pp. 83S. Abstract. Meeting Info: 25th European Symposium on Calcified Tissues. Harrogate, England, UK. (Apr. 25-29, 1997).*
Imazeki, et al, "Rapidly progressive renal failure model rat induced by adenine diet". J. Am. Soc. Nephrol. (2001). 12: A4267.
Koeda, et al, "Early changes of proximal tubles in the kidney of adenine-ingesting rats, with special reference to biochemical and electron microscopic studies". Japanese Journal of Nephrology. (1988). 30(3):239-246.
Moriguchi, et al, "Rapidly progressive secondary hyperparathyroidism due too renal failure in rats induced by adenine diet". J. Am. Soc. Nephrol. (2001) 12: A4301.
Mundy, G.R., "Factors which stimulate bone growth in vivo". Growth Regulation. (1993). 3:124-128.
Okada, et al, "Effect of rHuEPO on bone mineral density (BMD)". Proceedings of the 9th Congress on Kidney and Erythropoietin Study. (Oct. 28, 2000). Tokyo. pp. 37-41.
Yokazawa, et al, "Animal model of adenine-induced chronic renal failure in rats". Nephron. (1986). 44:230-234.
Yokozawa, et al, "Adenine-induced hyperuricemia and renal damage in rats". Nippon Nogeikagaku Kaishi (1982). 56(8):655-663.

* cited by examiner

*Primary Examiner*—Marianne P. Allen
*Assistant Examiner*—Regina M. DeBerry
(74) *Attorney, Agent, or Firm*—Browdy and Neimark, PLLC

(57) ABSTRACT

An agent for treatment of metabolic bone disease, which contains EPO as an active ingredient, or a method for treating a patient with metabolic bone disease, which comprises EPO, is provided. Pharmaceutical products containing EPO as the active ingredient are novel prophylactic and therapeutic agents which show an ameliorative action by healing bone and bone marrow lesions in bone disease, especially bone disease based on impaired bone metabolism, aside from the previously reported erythrocyte increasing action of EPO. Pathological states, targeted by these pharmaceutical products, are bone diseases showing metabolic bone disorders, including renal failure-associated osteodystrophy, marble bone disease, diabetic nephropathy, and osteoporosis.

4 Claims, 3 Drawing Sheets

AGENT FOR TREATMENT OF METABOLIC BONE DISEASE

TECHNICAL FIELD

This invention relates to an agent for treatment, and a method for treatment, of metabolic bone disease, especially, bone disease based on an abnormality in bone metabolism, the agent and method comprising erythropoietin (EPO) as the active ingredient.

BACKGROUND ART

With the aging of population and the prolongation of life in recent years, medical care concerned with metabolic bone disease has attracted great attention from the aspects of QOL and increasing medical costs. The metabolic bone disease, referred to herein, includes not only so-called regressive bone diseases, but also bone disease due to aging, and metabolic bone diseases which are complications of renal failure and diabetes closely related to lifestyle in modern times. Since metabolic bone diseases range widely, how to proceed with handling the diseases poses a major social challenge. With this social background, scientific findings about metabolic bone diseases have been rapidly accumulated since the latter half of the 1980s.

Therapies of metabolic bone diseases are intensively implemented in combination with therapeutic techniques and development of drugs. As a result, the multiphasic properties (redundancies) of different drugs have been found. For example, hematopoietic factors and bone metabolism-related drugs have correlate mechanisms of action, or show similar actions, thus suggesting that they are closely correlated. Investigation and establishment of methods for treatment of metabolic bone diseases, using model animals suffering from metabolic bone diseases, make it possible to provide useful information leading to improvement of QOL in patients with metabolic bone diseases.

Bone diseases include those which involve a high risk for bone fracture, such as osteoporosis indicated by a decrease in bone mineral content. For such bone diseases, diagnostic instruments using the bone mineral content as a parameter (bone mineral analyzers), intended for the prevention and diagnosis of these diseases, have been markedly developed and technologically improved, because of their noninvasiveness and convenience.

In regard to diagnosis of metabolic bone disease, bone morphometric diagnosis based on morphological observation using bone labeling was developed in the 1970s. However, this diagnostic technique has difficulty in convenience, and is not so widely used as the bone mineral analyzer in the clinical setting.

An adenine-induced nephropathy model rat (adenine model) is a model animal with chronic renal failure 1), 2), 3). According to a report4), the bone density (bone mineral content) of the femur of the model was measured by a bone mineral analyzer, with attention being focused on the relationship between the renal failure in this model and a decrease in bone mineral content. A tendency toward decrease was observed in the bone mineral content, and the administration of EPO in this pathological state was found to produce a tendency toward recovery in the bone mineral content.

We, the inventors of the present invention, had closely investigated the adenine model from the aspects of renal failure and its complications. Based on the results of the investigation, we reported that the adenine model, in which renal failure developed, was a pathological model animal showing a complication, such as secondary hyperparathyroidism, ectopic calcification, or renal osteodystrophy which is a metabolic bone disease, the complication similar to a complication of renal failure in humans 5, 6).

To look into the essence of metabolic bone disease, such as renal osteodystrophy, it is an absolute necessity to make a final analysis by a histopathological method based on a quantitative balance between osteoblasts and osteoclasts in bone tissue, which are cells relevant to bone metabolism, and functional changes and changes with time in these cells, with the conception of time being taken into consideration. The noninvasive diagnostic method based on measurement of the bone mineral content, when used singly, was merely enough to indicate a suspicion of osteoporosis, etc. which are some of metabolic bone diseases. This diagnostic method did not enable analysis of the exact nature of the relevant metabolic bone disease and estimate its essence.

DISCLOSURE OF THE INVENTION

In the case of a disease accompanied by a morphological change, as well as metabolic bone disease, a definitive diagnosis of its pathological state has to be made in consideration of quantitative parameters and histodiagnostic findings, which may cover diseases in other fields, for example, cancer. In this fact lies a scientific ground which justifies a histopathological diagnosis as a final diagnosis. In the present invention, this method is taken as the method of first choice, and an attempt is made to confirm, using this method, a preventive and therapeutic effect on metabolic bone disease which has not been successfully determined simply by the measurement of the bone mineral content.

An object of the present invention is to provide a preventive and therapeutic agent effective for prevention and treatment of impaired bone metabolism in a patient with renal failure.

We used the adenine model, and attempted to look into the essence of metabolic bone disease, and closely investigate the effect of EPO on bone metabolism, in this mode. For these purposes, we considered it necessary to make a final analysis based on a quantitative balance between osteoblasts and osteoclasts in bone tissue, which are cells relevant to bone metabolism, and functional changes and changes with time in these cells. With this consideration, we conducted a thorough histopathological search. As a result, we have found that the administration of EPO to the adenine model has the action of ameliorating impaired bone metabolism, especially, renal osteodystrophy, and have accomplished the present invention.

MODES FOR CARRYING OUT THE INVENTION

The present invention has found, as histopathological findings, the healing effect of EPO on a bone lesion in the adenine model which has not been successfully determined by a conventional noninvasive diagnostic technique for metabolic bone disease, for example, the measurement of the bone mineral content.

The adenine model is a model in which an adenine-containing diet is given for a certain period of time to induce an irreversible renal disorder, presenting with a pathological state of chronic renal failure. Beginning at 4 days after starting adenine feeding, 2,8-dihydroxyadenine, which is a metabolite of adenine, precipitates and crystallizes to form a deposit. Thus, obstruction occurs in the uriniferous tubule, causing a tissue disorder in the surroundings and leading to irreversible renal impairment. At a stage where chronic renal failure develops, a pathological state similar to a complication in a patient with chronic renal failure in human, such as anemia, renal osteodystrophy, secondary hyperparathyroidism, or ectopic calcification, is presented.

Diseases, for which EPO of the present invention is indicated, are bone diseases showing impairments in bone metabolism, including, for example, renal failure-associated osteodystrophy, marble bone disease, diabetic nephropathy, and osteoporosis.

EPO normalized the histopathological findings of impaired bone metabolism in renal osteodystrophy induced by adenine. The histopathological findings of the bone and bone marrow will be described below.

As will be mentioned in an Experimental Example, mild to severe renal osteodystrophy in the diaphysial cortical bone was observed in all adenine models used. At the metaphysis with moderate to severe osteodystrophy, two different characteristic histopathological findings were obtained.

Figure 1:
FIG. 1 is a photograph (8×, HE-stained) of a tissue specimen of the femoral metaphysis of adenine nephritis rats (solvent treatment group).
Figure 2:
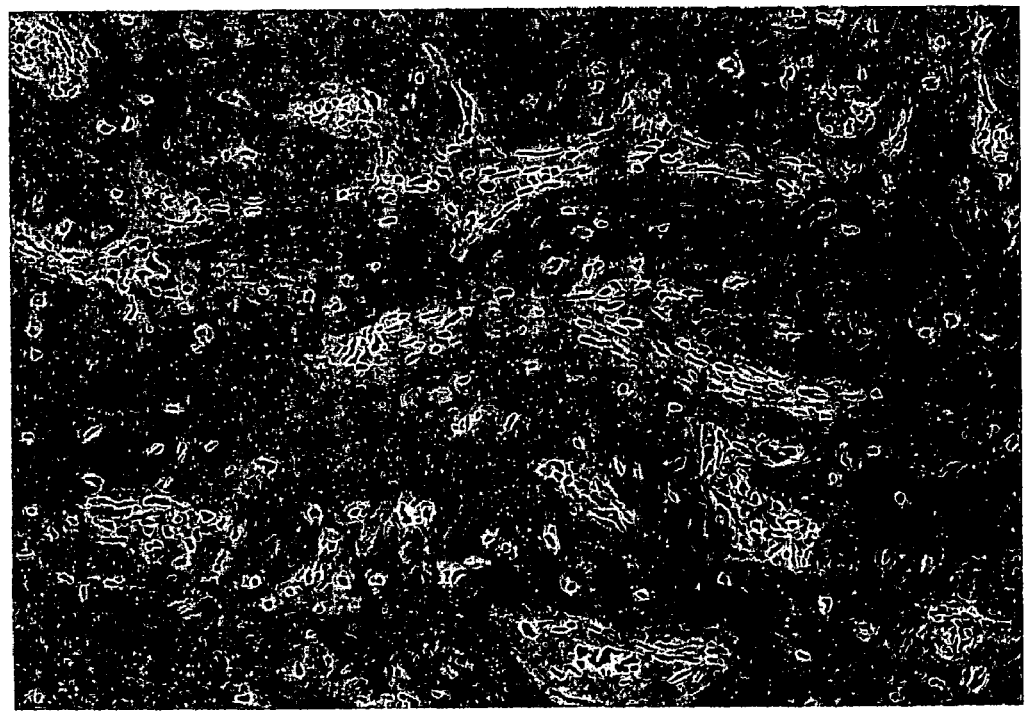
FIG. 2 is a photograph of the same tissue specimen as that in FIG. 1, however at a magnification of 80×.

A portion in the knee joint, ranging from the femoral metaphysis to an area closer to the diaphysis, (i.e., a cancellous proximal portion), showed persistence of primary cancellous bones, or increases in an immature bone matrix accompanied by osteoid formation, so as to form a border against the bone marrow. As noted here, there was no continuity with the diaphysial bone marrow, myeloid tissue was scant, and angiogenesis was rare (FIG. 1). In these cancellous bones, osteoblasts were seen, while osteoclasts were scarcely observed, and bone resorption was stagnant, with the result that bone metabolism was delayed, and a cartilage matrix remained (FIG. 2). Between the lesions in the cancellous proximal portion and the epiphysial cartilage (cancellous distal portion), typical cancellous bone tissues with osteodystrophy, which comprised osteoclasts, osteoblasts, and fibroblasts around the cancellous bones, were observed transversely and in band form with respect to the long axis, although their numbers were small (FIG. 1).

Figure 3:
FIG. 3 is a photograph (8×, HE-stained) of a tissue specimen of the femoral metaphysis of adenine nephritis rats (EPO treatment group).
Figure 4:
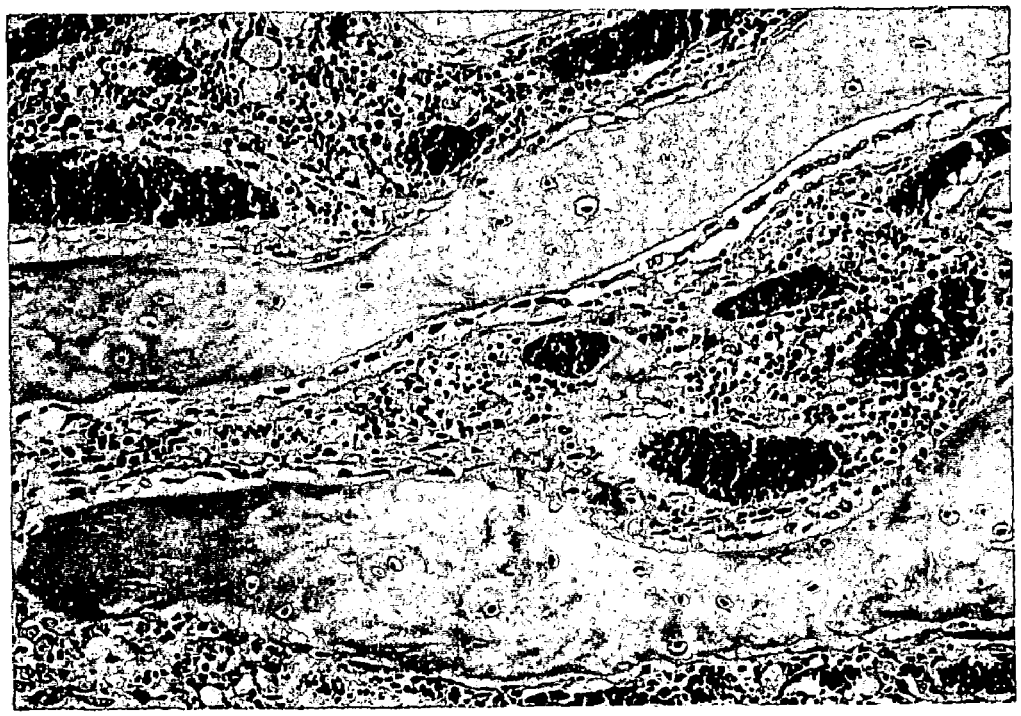
FIG. 4 is a photograph of the same tissue specimen as that in FIG. 3, however at a magnification of 80×.

Following treatment with EPO, bone resorption cavities by osteoclasts and increases in activated osteoblasts were observed on the surfaces of bones in both of the cancellous proximal portion and the cancellous distal portion. Simultaneously, angiogenesis for entry of erythrocytes was noted in many sites of the medullary cavities (FIG. 3). Such erythrocyte increases within the blood vessels were observed within diaphysial cortical bones and in microvessels of bone resorption cavities. Fibroblasts remained around the cancellous bones, but activated osteoclasts and osteoblasts were observed, and the bone matrix was thinned to form laminar bones, which were observed as mature cancellous bones (FIG. 4).

The histopathologically improving effects of EPO treatment for bone and bone marrow lesions in adenine models are summarized as follows: In adenine models, renal lesions occurred several days after ingestion of adenine through feeding. Bone metabolism impairments were also induced at an early stage owing to increases in blood phosphorus values, decreases in activated VD, accelerated production of PTH, etc. These bone lesions were divided into two types at the cancellous bones. Bone metabolism impairments during the 4 weeks, which were the initial period of ingestion of adenine through feeding, were seen in the cancellous distal portion, and were observed as increases in osteoid tissues and persistence of the bone matrix owing to delay in remodeling based on the decline in bone resorption. Subsequently, there was transient normalization of renal function in a 4-week period after replacement by a normal diet. During this period, lesions characterized by osteitis fibrosa were observed in the cancellous proximal portion where bone metabolism takes place. These changes in metabolic bone disorders over time, which were observed in both cancellous bone portions, were induced by changeover of the diet. EPO was administered during the 4-week period as the latter half of the study and, following this EPO treatment, erythropoiesis was accelerated in the bone marrow, and many veins (sinusoids) full of and hyperemic with many erythrocytes were observed. Treatment with EPO is assumed to have induced the acceleration of erythropoiesis, angiogenesis based on stimulation of VEGF production, survival of hematopoietic stem cells from diaphysial bone marrow, and initiation of bone resorption due to influx of preosteoclasts, and bone formation induced thereby. Finally, following EPO treatment, cancellous bones with metabolic bone disorders over time, which were observed in both cancellous bone portions, formed mature laminar bones, and the convalescent tendency of myeloid tissue proceeded simultaneously. Thus, healing of lesions in both of bone tissue and myeloid tissue was observed histopathologically.

Figure 5:
FIG. 5 is a photograph (8×, HE-stained) of a tissue specimen of the femoral metaphysis of normal rats.
Figure 6:
FIG. 6 is a photograph (8×, HE-stained) of a tissue specimen of the femoral metaphysis of normal rats (EPO treatment group).

Treatment with EPO in normal rats (FIG. 5), on the other hand, produced no marked morphological changes (FIG. 6).

As erythropoietin (EPO), which is the active ingredient used in the present invention, there can be named, for example, natural human EPO obtained by extraction from the urine of patients with human aplastic anemia (Japanese Patent Publication No. 1989-38,800); and EPO products manufactured by genetic recombination technologies which comprise collecting messenger RNA (mRNA) corresponding to the amino acid sequence of human EPO, constructing recombinant DNA with the use of the mRNA, and then causing suitable hosts (e.g., microorganisms such as *Escherichia coli*, yeasts, cell strains of plants, and cell strains of animals, such as COS cells, Chinese hamster ovarian cells (CHO), and mouse C-127 cells) to produce EPO from the recombinant DNA [for example, Japanese Patent Publication No. 1989-44317; Kenneth Jacobs et al., Nature, 313, 806–810 (1985)].

EPO usable in the present invention may be those of the above-mentioned origins, and their modifications. EPO modification products include, for example, those described in Japanese Patent Application Laid-Open No. 1991-151399. Among these EPO modification products are those in which Asn in the peptide chain of the original glycoprotein has been mutated to Gln, and the number of bindings of N-linked sugar chains bound has been changed. As other amino acid mutations, those described in Japanese Patent Application Laid-Open No. 1990-59599 and Japanese Patent Application Laid-Open No. 1991-72855 are named. That is, there may be any number of amino acid mutations, deletions, or additions, unless the property of EPO acting on the EPO receptor is lost.

In regard to preparations containing EPO of the present invention as the active ingredient, suspending agents, solution adjuvants, stabilizers, tonicity agents, preservatives, and adsorption preventing agents may be added, if desired, depending on the methods of administering them and their dosage forms. Examples of the suspending agents are methylcellulose, polysorbate 80, hydroxyethylcellulose, acacia, tragacanth powder, sodium carboxymethylcellulose, and polyoxyethylene sorbitan monolaurate. Examples of the solution adjuvants are polyoxyethylene hydrogenated castor oil, polysorbate 80, nicotinamide, polyoxyethylene sorbitan monolaurate, macrogol, and castor oil fatty acid ethyl ester. Examples of the stabilizers are human serum albumin, dextran 40, methylcellulose, gelatin, sodium sulfite, and sodium metasulfite. Examples of the tonicity agents are D-mannitol and sorbitol. Examples of the preservatives are methyl parahydroxybenzoate, ethyl parahydroxybenzoate, sorbic acid, phenol, cresol, and chlorocresol. Examples of the adsorption preventing agents are human serum albumin, lecithin, dextran, ethylene oxide-propylene oxide copolymer, hydroxypropylcellulose, methylcellulose, polyoxyethylene hydrogenated castor oil, and polyethylene glycol.

By using the EPO of the present invention as the active ingredient and adding a certain amino acid as a stabilizer, a stable EPO solution preparation free from human serum albumin or purified gelatin can be used. This stable EPO solution preparation is described in Japanese Patent Application Laid-Open No. 1998-182481. The descriptions in this publication are to be included in a part of the specification of the present application.

The amino acid added as the stabilizer in this EPO solution preparation includes free amino acids, and their salts such as sodium salts, potassium salts and hydrochlorides. To the solution preparation of the present invention, one of these amino acids can be added, or two or more of these amino acids can be added in combination. The preferred amino acids are leucine, tryptophan, serine, glutamic acid, arginine, histidine, and lysine, each in D-, L- and DL-forms, and their salts. More preferred are L-leucine, L-tryptophan, L-glutamic acid, L-arginine, L-histidine, and L-lysine, and their salts. Particularly preferred are L-arginine, L-histidine, and L-lysine, and their salts. The most preferred are L-histidine, and its salts.

Details of the method, etc. for producing the above-described stable EPO solution preparation are as described in the aforementioned publication.

The dose of these EPO products in prophylactic and therapeutic drugs targeted by the present invention can be determined, as appropriate, in consideration of the disease to be dealt with, its symptoms and so forth. The dose is usually 0.1 to 500 μg, preferably 5 to 100 μg, per adult.

Hereinbelow, the present invention will be described in further detail by Experimental Example and Examples, but the present invention is in no way limited by the Experimental Example and Examples. In the Experimental Example, the effects of the present invention were confirmed.

EXPERIMENTAL EXAMPLE (Experimental animals)
Male Wistar rats (Charles River Japan) were introduced at 5 weeks of age, acclimatized for 2 weeks, and then subjected to experiments at 7 weeks of age.

(Drugs for Treatment and Treatment Schedule)

(1) Drugs for Treatment
EPO: Epogin Injection 3000 (Epoetin β, CHUGAI PHARMACEUTICAL). This preparation was diluted to 200 IU/mL with a vehicle.
Vehicle: 1 mM phosphate buffer (pH 7.4) containing 0.25% gelatin and 1.25% D-mannitol
Adenine: A mixed solid diet, comprising the composition of a rat normal solid sample (CE-2, CLEA JAPAN) and containing adenine (6-aminopurine) at a weight ratio of 0.75%, was prepared (CLEA JAPAN), and used as an adenine-mixed feeding sample.

(2) Treatment Groups
The following treatment groups were established:
Adenine vehicle treatment group:
The adenine sample was given as a diet, and the vehicle was administered.
Adenine EPO treatment group:
The adenine sample was given as a diet, and EPO was administered.
CE-2 group:
A normal diet was given, and neither vehicle nor EPO was administered.

(3) Treatment Schedule
The day when the adenine feeding began was taken as Day 0.
In the adenine vehicle treatment group and the adenine EPO treatment group, adenine was administered as the adenine-mixed feeding sample for 4 weeks after start of experiments. The normal diet was given for 4 weeks, from the 5th week to the 8th week, after start of experiments. The CE-2 group received the normal diet from the start of experiments until completion of the experiments.

EPO was administered subcutaneously to the back (neck back), at a dose of 200 IU/kg three times weekly, for 4 weeks from the 5th week to the 8th week after start of the experiments. The vehicle was administered subcutaneously to the back 3 times weekly for 4 weeks from the 5th week to the 8th week after start of the experiments. The amount of the EPO or vehicle administered as a liquid was 1 mL/kg.

(Collection of Organs)
Dissection was performed 8 weeks after the start of the experiments to remove the kidneys, parathyroid glands, and femurs, and these organs were fixed in formalin.

(Preparation of Tissue Specimen)
After fixation in formalin, the femur was decalcified. The kidney, the parathyroid gland, and the decalcified femur were embedded in paraffin, and paraffin sections were prepared. Each of the sections was stained with hematoxylin-eosin(HE), and studied histopathologically.

(Results)
The Wistar rats were fed the adenine-mixed feeding sample for 4 weeks, and then fed the normal diet for 4 weeks. By this procedure, varieties of lesions were observed in the kidney, such as tubular dilatation, urinary casts, degenerative atrophy of the tubular epithelium, epithelial growth accompanied by giant cell formation, and interstitial hypertrophy accompanied by cellular infiltration. These are histopathological findings meaning renal dysfunction due to adenine feeding. These findings were observed diffusely from a moderate to severe degree. The parathyroid gland showed proliferative hypertrophy in all adenine models observed, and glandular cell division images were observed in many individuals. The animals fed the normal diet showed no such changes. The proliferative hypertrophy found in the parathyroid gland showed no influence by EPO treatment.

In connection with the bone and the bone marrow, mild to severe renal osteodystrophy in the diaphysial cortical bone was observed in all adenine models. At the metaphysis with moderate to severe osteodystrophy, two different characteristic histopathological findings were obtained.

A portion in the knee joint, ranging from the femoral metaphysis to an area closer to the diaphysis, (i.e., a cancellous proximal portion), showed persistence of primary cancellous bones, or increases in an immature bone matrix accompanied by osteoid formation, so as to form a border against the bone marrow. There was no continuity with the diaphysial bone marrow, myeloid tissue was scant, and angiogenesis was rare (FIG. 1). In these cancellous bones, osteoblasts were seen, while osteoclasts were scarcely observed, and bone resorption was stagnant, with the result that bone metabolism was delayed, and a cartilage matrix remained (FIG. 2). Between these lesions in the cancellous proximal portion and the epiphysial cartilage (cancellous distal portion), typical cancellous bone tissues with osteodystrophy, which comprised osteoclasts, osteoblasts, and fibroblasts around the cancellous bones, were observed transversely and in band form with respect to the long axis, although their numbers were small.

Following treatment with EPO, bone resorption cavities by osteoclasts and increases in activated osteoblasts were observed on the surfaces of bones in both of the cancellous proximal portion and the cancellous distal portion. Simultaneously, angiogenesis for filling the lumen with erythrocytes was noted in many sites of the medullary cavities (FIG. 3). Such erythrocyte increases within the blood vessels were also observed within diaphysial cortical bones and in microvessels of bone resorption cavities. Fibroblasts remained around the cancellous bones, but activated osteoclasts and osteoblasts were observed, and the bone matrix was thinned to form laminar bones, which were observed as mature cancellous bones (FIG. 4).

The histopathologically improving effects of EPO treatment on bone and bone marrow lesions in adenine models are summarized as follows: In adenine models, renal lesions occurred several days after ingestion of adenine through feeding. Bone metabolism impairments were also induced at an early stage owing to increases in blood phosphorus values, decreases in activated VD, accelerated production of PTH, etc. These bone lesions are divided into two types at the cancellous bones. Bone metabolism impairments during the 4 weeks, which were the initial period of ingestion of adenine through feeding, were noted in the cancellous distal portion, and were observed as increases in osteoid tissues and persistence of the bone matrix owing to delay in remodeling based on the decline in bone resorption. Subsequently, there was transient normalization of renal function in the 4-week period after replacement by the normal diet. During this period, lesions characterized by osteitis fibrosa were observed in the cancellous proximal portion where bone metabolism takes place. These changes in metabolic bone disorders over time, which were observed in both cancellous bone portions, were induced by changeover of the diet. EPO was administered during the 4-week period as the latter half of the study and, following this EPO treatment, erythropoiesis was accelerated in the bone marrow, and many veins (sinusoids) full of and hyperemic with many erythrocytes were observed. Treatment with EPO is assumed to have induced the acceleration of erythrocyte proliferation, angiogenesis based on stimulation of VEGF production, survival of hematopoietic stem cells from diaphysial bone marrow, initiation of bone resorption due to influx of preosteoclasts, and osteogenesis induced thereby. Finally, following EPO treatment, cancellous bones with metabolic bone disorders over time, which were observed in both cancellous bone portions, formed mature laminar bones, and the convalescent tendency of myeloid tissue proceeded simultaneously. Thus, healing of lesions in both of bone tissue and myeloid tissue was observed histopathologically.

Treatment with EPO in normal rats (FIG. 5), on the other hand, produced no marked morphological changes (FIG. 6).

Examples concerned with pharmaceutical manufacturing will be shown below.

EXAMPLE 1

| | |
|---|---|
| Erythropoietin | 8 μg |
| Total amount made with distilled water for injection | 2 ml |

A solution was aseptically prepared from the above formulation. The resulting solution was dispensed in a vial, and sealed up.

EXAMPLE 2

| | |
|---|---|
| Erythropoietin | 8 μg |
| Total amount made with distilled water for injection | 2 ml |

A solution was aseptically prepared from the above formulation. The resulting solution was dispensed in a vial, lyophilized, and sealed up.

EXAMPLE 3

| | |
|---|---|
| Erythropoietin | 16 μg |
| Total amount made with distilled water for injection | 2 ml |

A solution was aseptically prepared from the above formulation. The resulting solution was dispensed in a vial, and sealed up.

EXAMPLE 4

| | |
|---|---|
| Erythropoietin | 16 μg |
| Total amount made with distilled water for injection | 2 ml |

A solution was aseptically prepared from the above formulation. The resulting solution was dispensed in a vial, lyophilized, and sealed up.

EXAMPLE 5

| Erythropoietin | 8 μg |
|---|---|
| Human serum albumin | 5 mg |
| Total amount made with distilled water for injection | 2 ml |

A solution was aseptically prepared from the above formulation. The resulting solution was dispensed in a vial, and sealed up.

EXAMPLE 6

| Erythropoietin | 8 μg |
|---|---|
| Human serum albumin | 5 mg |
| Total amount made with distilled water for injection | 2 ml |

A solution was aseptically prepared from the above formulation. The resulting solution was dispensed in a vial, lyophilized, and sealed up.

EXAMPLE 7

| Erythropoietin | 16 μg |
|---|---|
| Human serum albumin | 5 mg |
| Total amount made with distilled water for injection | 2 ml |

A solution was aseptically prepared from the above formulation. The resulting solution was dispensed in a vial, and sealed up.

EXAMPLE 8

| Erythropoietin | 16 μg |
|---|---|
| Gelatin | 5 mg |
| Total amount made with distilled water for injection | 2 ml |

A solution was aseptically prepared from the above formulation. The resulting solution was dispensed in a vial, lyophilized, and sealed up.

EXAMPLES 9 to 12

Injections were prepared in the same manner as in Examples 5 to 8, except that 5 mg of dextran 40 was used instead of human serum albumin used in Examples 5 to 8.

EXAMPLE 13

D-Mannitol (5 g), 1 mg of erythropoietin, and 100 mg of human serum albumin were aseptically dissolved in 100 ml of distilled water for injection to prepare an aqueous solution. The aqueous solution (1 ml) was dispensed in a vial, lyophilized, and sealed up.

EXAMPLE 14

A solution (1 ml) containing the following ingredients was prepared:

| EPO | 1,500 IU |
|---|---|
| Nonionic surfactant (Polysorbate 80: Nikko Chemicals) | 0.05 mg |
| Sodium chloride | 8.5 mg |
| L-Arginine hydrochloride (Sigma) | 10 mg |

This solution was adjusted to pH 6.0 with a 10 mM phosphate buffer solution (Wako Pure Chemical Industries), and 1 ml of the solution was charged into a 5 ml glass vial. The glass vial was stoppered, and sealed to produce a solution preparation.

EXAMPLE 15

A solution preparation was produced in the same manner as in Example 14 from a solution containing the following ingredients in 1 ml:

| EPO | 1,500 IU |
|---|---|
| Nonionic surfactant (Polysorbate 80: Nikko Chemicals) | 0.05 mg |
| Sodium chloride | 8.5 mg |
| L-Histidine hydrochloride (Sigma) | 10 mg |

EXAMPLE 16

A solution preparation was produced in the same manner as in Example 14 from a solution containing the following ingredients in 1 ml:

| EPO | 1,500 IU |
|---|---|
| Nonionic surfactant (Polysorbate 80: Nikko Chemicals) | 0.05 mg |
| Sodium chloride | 8.5 mg |
| L-Lysine hydrochloride (Sigma) | 10 mg |

INDUSTRIAL APPLICABILITY

Pharmaceutical products containing EPO as the active ingredient, according to the present invention, are novel prophylactic and therapeutic agents which show an ameliorative action by healing bone and bone marrow lesions in bone disease, especially bone disease based on impaired bone metabolism, aside from the previously reported erythrocyte increasing action of EPO. Pathological states, targeted by these pharmaceutical products, are bone diseases showing metabolic bone disorders, including renal failure-associated osteodystrophy, marble bone disease, diabetic nephropathy, and osteoporosis.

REFERENCES

1) Yokosawa, T., Oura, H., Nakagawa, H., Okada, T. Elevation of serum uric acid levels and renal function disorder by long-term administration of adenine. Journal of The Agricultural Chemical Society of Japan, 56:655–663(1982).

2) Koeda, T., Wakaki, K., Koizumi, F., Yokozawa, T., Oura, H. Early changes of proximal tubules in the kidney of adenine-ingesting rats, with special reference to biochemical and electron microscopic studies. Jpn. J. Nephrol., 30:1–8(1988).
3) Yokozawa, T., Zheng, P. D., Oura, H., Koizumi, F. Animal model of adenine-induced chronic renal failure in rats. Nephron, 44:230–234(1986).
4) Okada, H., Kaneko, Y., Furukawa, K., Yawata, T., Motomiya, Y. Effect of rHuEPO on bone mineral density (BMD). Proceedings of the 9th Congress on Kidney and Erythropoietin Study: 37–41(2001)
5) Ohkawa, H., Imazeki, I., Moriguchi, Y., Imai, N., Matsubara, S., Saito, M. Rapidly progressive secondary hyperparathyroidism due to renal failure in rats induced by adenine diet. J. Am. Soc. Nephrol., 12: 822A(2001).
6) Imazeki, I., Ohkawa, H., Moriguchi, Y., Imai, N., Matsubara, S., Saito, M. Rapidly progressive renal failure model rat induced by adenine diet. J. Am. Soc. Nephrol., 12:816A(2001).

The invention claim is:

1. A method of treatment of renal failure-associated metabolic bone disease, comprising administering an effective amount of erythropoietin for said treatment to a patient with renal failure-associated metabolic bone disease.

2. The method of treatment according to claim 1, comprising administering erythropoietin in a usual dose of 0.1 to 500 µg, per adult.

3. The method of claim 2 wherein said usual dose is 5 to 100 µg.

4. The method of treatment according to claim 1 wherein said patient with said renal failure-associated metabolic bone disease is a patient with renal failure-associated osteodystrophy or renal failure-associated osteoporosis.

* * * * *